United States Patent
Stepanski et al.

(10) Patent No.: US 10,058,795 B2
(45) Date of Patent: Aug. 28, 2018

(54) PROCESS AND APPARATUS FOR PURIFICATION OF A STREAM CONTAINING A CYCLIC ESTER OF AN ALPHA-HYDROXYCARBOXYLIC ACID

(71) Applicants: Sulzer Chemtech AG, Winterthur (CH); Futerro S.A., Escanaffles (BE)

(72) Inventors: Manfred Stepanski, Buchs (CH); Peter Fässler, Allschwil (CH); Philippe Coszach, Courcelles (BE)

(73) Assignees: Sulzer Chemtech AG, Winterthur (CH); Futerro S.A., Escanaffles (BE)

( * ) Notice: Subject to any disclaimer, the term of this patent is extended or adjusted under 35 U.S.C. 154(b) by 327 days.

(21) Appl. No.: 14/773,697

(22) PCT Filed: Feb. 4, 2014

(86) PCT No.: PCT/EP2014/052154
§ 371 (c)(1),
(2) Date: Sep. 8, 2015

(87) PCT Pub. No.: WO2014/139730
PCT Pub. Date: Sep. 18, 2014

(65) Prior Publication Data
US 2016/0024043 A1     Jan. 28, 2016

(30) Foreign Application Priority Data

Mar. 11, 2013 (EP) .................................... 13158539

(51) Int. Cl.
*B01D 3/14* (2006.01)
*C07D 319/12* (2006.01)
(Continued)

(52) U.S. Cl.
CPC ............... *B01D 3/14* (2013.01); *B01D 1/065* (2013.01); *B01D 3/02* (2013.01); *B01D 3/143* (2013.01);
(Continued)

(58) Field of Classification Search
CPC .......... B01D 1/065; B01D 3/14; B01D 3/143; B01D 3/148; B01D 9/0031; B01D 9/004
See application file for complete search history.

(56) References Cited

U.S. PATENT DOCUMENTS

| 4,835,293 A | 5/1989 | Bhatia |
| 5,236,560 A | 8/1993 | Drysdale et al. |

(Continued)

FOREIGN PATENT DOCUMENTS

| WO | 96/06092 A1 | 2/1996 | | |
| WO | WO 2012/069704 | * | 5/2012 | ............. C11B 13/00 |
| WO | WO 2012/110117 | * | 8/2012 | ............... B01D 7/00 |

*Primary Examiner* — Renee E Robinson
(74) *Attorney, Agent, or Firm* — Larson & Anderson, LLC (57) ABSTRACT

The invention relates to a process for purification of a stream containing a cyclic ester of an alpha-hydroxycarboxylic acid of formula (I), wherein each R independently represents hydrogen or an aliphatic hydrocarbon having 1 to 6 carbon atoms comprising the steps of: (a) separating the cyclic ester-containing stream into one or more cyclic ester-containing vapor fractions and one or more cyclic ester-containing liquid fractions; (b) condensing a cyclic ester-containing vaporized fraction as obtained in step (a) to obtain a cyclic ester-containing condensate; (c) subjecting at least part of the cyclic ester-containing condensate as obtained in step (b) to melt crystallization to obtain a purified cyclic ester-containing stream and a residue stream; and (d) recovering the purified cyclic ester-containing stream as obtained in step (c). The invention further relates to an apparatus suitable for carrying out the present process.

18 Claims, 2 Drawing Sheets

(51) Int. Cl.
*B01D 9/00* (2006.01)
*B01D 1/06* (2006.01)
*B01D 3/02* (2006.01)

(52) U.S. Cl.
CPC ............ *B01D 3/148* (2013.01); *B01D 9/004* (2013.01); *B01D 9/0031* (2013.01); *C07D 319/12* (2013.01); *B01D 2009/0086* (2013.01)

(56) References Cited

U.S. PATENT DOCUMENTS

| | | |
|---|---|---|
| 5,357,034 A | 10/1994 | Fridman et al. |
| 5,504,247 A | 4/1996 | Saxer et al. |
| 5,521,278 A | 5/1996 | O'Brien et al. |
| 5,900,491 A | 5/1999 | Kurashima et al. |
| 8,053,584 B2 * | 11/2011 | Meerdink ............ C07D 319/12 203/99 |

* cited by examiner

Fig.1

Fig.2

PROCESS AND APPARATUS FOR PURIFICATION OF A STREAM CONTAINING A CYCLIC ESTER OF AN ALPHA-HYDROXYCARBOXYLIC ACID

FIELD OF THE INVENTION

The present invention relates to a process for purification of stream containing a cyclic ester of an alpha-hydroxycarboxylic acid, in particular a lactide-containing stream. The present invention further relates to an apparatus for purification of a stream containing a cyclic ester of an alpha-hydroxycarboxylic acid which can be used in the present process.

BACKGROUND OF THE INVENTION

As concerns for the environment grow, biodegradable polymers are becoming of increasing commercial interest as a substitute for conventional and less degradable synthetic polymers such polyolefins and polyurethanes. The use of biodegradable polymers in areas of packaging and textiles is therefore steadily growing. Consequently, much research is directed to the synthesis of these biodegradable materials. Among the various biodegradable polymers, polylactide (PLA) is one of the most commonly used and studied.

PLA is an aliphatic polyester based on lactic acid, the latter being obtained by fermentation of sugars and/or starch. PLA is therefore derived from renewable vegetables and is biodegradable by composting.

PLA is prepared from lactide by ring-opening polymerization. Lactide which is a dimeric cyclic ester of lactic acid can in turn be formed by dehydrating aqueous lactic acid to form a mixture of oligomers, which mixture is then depolymerised to form lactide.

A number of other processes exist for preparing lactide. In U.S. Pat. No. 5,900,491, a process is described in which lactide is synthesized from DL-methyl lactate material by addition of methyl orthoformate. The aim of said process is to provide high-purity lactide containing small amounts of impurities such as water and an acid component. Further, in U.S. Pat. No. 4,835,293, a process is disclosed for preparing highly pure cyclic esters such as lactide by heating a polymer of the corresponding alpha-hydroxy acid or its ester or a copolymer of the alpha-hydroxy acid or its ester and a thermally stable polyether core in the presence of an inert gas with the cyclic ester being carried from this reaction with the inert gas to a solvent system.

The lactide may as such have one of three types of optical activity depending whether it consists of two L-lactic acid molecules, two D-lactic acid molecules or an L-lactic acid molecule and a D-lactic acid molecule combined to form the dimer. These three types of dimers are known as L-lactide, D-lactide and meso-lactide respectively.

In order to prepare PLA of a high quality it is very important to use lactide of a high purity. The lactide needs therefore to be purified to a high extent before ring-opening polymerization may take place to prepare PLA of a high quality. In practice this means that the lactide needs to be free from water and impurities such as lactic acid, oligomers of lactic acid, catalyst, and light and heavy colour impurities as for instance sugars, nutrients, proteins and amino acids.

A variety of lactide purification processes are known that usually comprise one or more integrated distillation, condensation and crystallization steps. It is known in the art that crystallization processes or methods may be typically carried out in multiple stages such as falling film crystallization, suspension melt crystallization or static crystallization stages. U.S. Pat. No. 5,504,247 discloses such a crystallization method for the purification of acrylic acid. Similarly purification apparatuses may comprise different types of crystallization sub-units such as falling film crystallization, suspension melt crystallization or static crystallization sub-units. Additional information on crystallizers and their operation is disclosed in Handbook of Industrial Crystallization, 2nd Edition, by Allan S. Myerson, published Jan. 9, 2002 by Butterworth-Heinemann, Woburn, Mass. ISBN: 978-0750670128 and Crystallization Technology Handbook, 2nd Edition, edited by A. Mersmann, published 2001 by Marcel Dekker, Basel, ISBN: 0-8247-0528-9.

In U.S. Pat. No. 5,521,278, an integrated process for the manufacture of lactide is described in which aqueous lactic acid is first dehydrated in at least two stages to effect condensation polymerization of the lactic acid and the formation of oligomers. The oligomers formed are thermally cracked in the presence of a depolymerisation catalyst to form lactide vapour. The lactide vapour is then condensed and the condensate is vacuum fractionally distilled whereby lactic acid, water and lactide are removed as vapour overhead, whereas concentrated lactide is removed as a liquid side stream and heavy ends are removed as molten liquid. The liquid side stream of concentrated lactide is then subjected to melt crystallization to separate purified lactide having an acidity potential less than 6 meq/kg of lactide from a residual lactide having an acidity potential of at least 30 meq/kg.

In U.S. Pat. No. 5,357,034, a lactide polymerization process is described which comprises the steps of: (i) dehydrating aqueous lactic acid and polymerizing lactic acid by condensation to; (ii) heating and reacting an equilibrium mixture comprising mainly polylactic acid and small amounts of water, lactic acid, lactide and linear oligomers of lactic acid, and depolymerising polylactic acid to form lactide; (iii) distilling off a vapour phase comprising mainly lactide, lactic acid, linear oligomers of lactic acid and water; (iv) further fractionating in a separate unit operation the distillate obtained in the step (iii) into crude lactide and a distillate phase, comprising in addition to lactide, water, lactic acid, and linear oligomers, which is optionally recycled to step (i); and (v) purifying the crude lactide as obtained in step (iv) by melt crystallization; and (vi) bulk or solution polymerizing the purified lactide.

These known processes leave, however, room for improvement in terms of purity of the lactide obtained and condensation and crystallization efficiency.

It is therefore object of the present invention to provide a process for purification of a cyclic ester of an alpha-hydroxycarboxylic acid in which in particular a lactide of a higher purity and lighter colour is obtained and at the same time a more efficient condensation and melt crystallization is realized.

SUMMARY OF THE INVENTION

It has now been found that this can be established when a cyclic ester of an alpha-hydroxycarboxylic acid-containing vapour, instead of a liquid cyclic ester of an alpha-hydroxycarboxylic acid stream, is withdrawn from a separation unit via a side draw and said vapour is subsequently condensed before the condensate obtained is subjected to melt crystallization.

Accordingly, the present invention relates to a process for purification of a stream containing a cyclic ester of an alpha-hydroxycarboxylic acid of formula (I)

formula (I)

wherein each R independently represents hydrogen or an aliphatic hydrocarbon having 1 to 6 carbon atoms comprising the steps of:
(a) separating the stream containing the cyclic ester into one or more cyclic ester-containing vapour fractions and one or more cyclic ester-containing liquid fractions;
(b) condensing a cyclic ester-containing vapour fraction as obtained in step (a) to obtain a cyclic ester-containing condensate;
(c) subjecting at least part of the cyclic ester-containing condensate as obtained in step (b) to melt crystallization to obtain a purified cyclic ester-containing stream and a residue stream; and
(d) recovering the purified cyclic ester-containing stream as obtained in step (c).

Even if the liquid stream of lactide is withdrawn from a distillation column via a side drawn and subsequently subjected to a crystallisation step such as described in U.S. Pat. No. 5,521,278, the process in accordance with the present invention is highly advantageous when compared to such known process.

The present process is highly attractive since it allows for (i) less thermal degradation of cyclic ester prior to melt crystallization; (ii) more efficient condensation and melt crystallization steps; and (iii) the production of a cyclic ester having a higher purity and a reduced colour.

DETAILED DESCRIPTION OF THE INVENTION

The present invention provides a process for purification of a cyclic ester-containing stream.

In formula (I) of the cyclic esters to be purified according to the invention, R represents H or an aliphatic hydrocarbon having from 1 to 6 carbon atoms. The aliphatic hydrocarbon may be a linear or branched hydrocarbon. Preferably, the cyclic ester of the alpha-hydroxycarboxylic acid is lactide or glycolide, more preferably lactide. In the context of the present invention the term "lactide" refers to any of L-lactide, D-lactide, and meso-lactide, and any mixture thereof. Hence, the purified lactide to be obtained in accordance with the present invention may comprise L-lactide, D-lactide, meso-lactide and/or any mixture thereof.

In accordance with the present invention the source of the lactide-containing stream may vary. For example, the stream may come from a lactide production, from a recycled lactide or PLA, or from the devolatilization of PLA. In this respect it is observed that the lactide from which PLA can be prepared may be obtained by various routes of synthesis. The lactide-containing stream to be purified can, for instance, prepared by a two-step polymerization/depolymerisation process, in which first lactic acid from a feed source is polymerized to a relatively low molecular weight polylactic acid which polylactic acid is then heated, generally in the presence of a catalyst, to depolymerise the low molecular weight polylactic acid to lactide. The lactide will usually be recovered as a component of a vapour product stream, which stream will also contain water and impurities such as lactic acid, oligomers of lactic acid, catalyst, and light and heavy colour impurities. These impurities need to be removed from the vapour product stream in order to obtain a lactide of high purity and good colour.

Although the present invention will in particular be discussed in respect of lactide, the skilled person would immediately understand that the present invention also applies to other cyclic esters such as glycolide. It is also understood that in case of glycolide the volatile impurities will include glycolic acid, whereas the less volatile impurities would include polyglycolide oligomers.

The lactide-containing stream to be purified in accordance with the present process may comprise L-lactide, D-lactide, meso-lactide and mixtures thereof, as indicated hereinbefore.

Suitably, step (a) is carried out in a separation unit such as a distillation column. Preferably, the distillation column is a multi-stage distillation column, more preferably a rectification column. The rectification column can be any type of known rectification column such as a tray column or a packed column. Preferably, the rectification column is a packed column or a tray column. When use is made of a tray column, the tray column suitably comprises a number of theoretical stages (NTS) in the range of from 6-30, preferably a number of theoretical stages in the range of from 10-16.

The separation in step (a) is suitably carried out at a temperature in the range of from 80-200° C., preferably in the range of from 80-180° C., more preferably in the range of from 100-160° C., and a pressure in the range of from 3-50 mbara, preferably in the range of from 7-20 mbara.

The separation in step (a) is suitably carried out at a temperature in the range of from 80-180° C. and a pressure in the range of 3-50 mbara. Preferably, the separation in step (a) is carried out at a temperature in the range of from 100-160° C. and a pressure in the range of 7-20 mbara.

Figure 1:
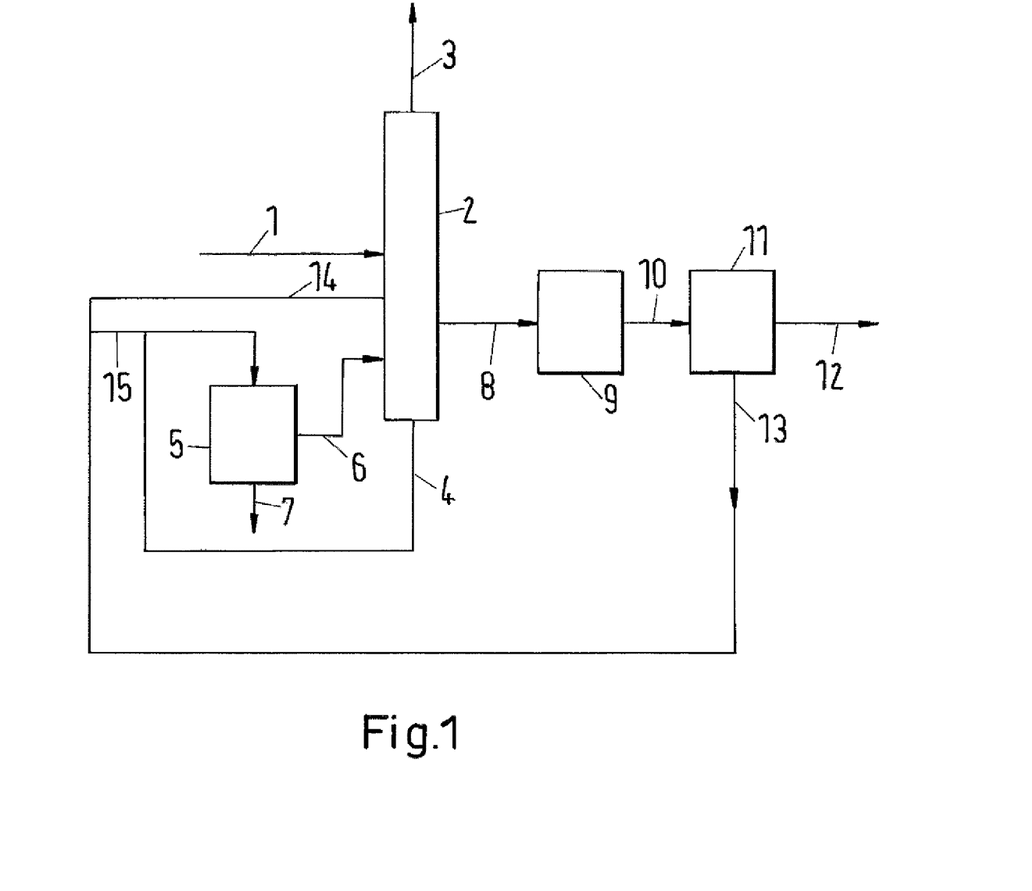

One embodiment of the present invention is illustrated in FIG. 1.

In FIG. 1, a lactide-containing stream is led via line 1 to rectification column 2. In rectification column 2, the lactide-containing stream is subjected to a multi-step fractionation process, thereby obtaining more volatile components such as water, lactic acid and less volatile components such as liquid lactide and oligomers of lactic acid. The more volatile components are withdrawn from rectification column 2 via line 3, whereas less volatile components will move to the lower part of the rectification column. In the lower part of the rectification column a lactide-containing liquid fraction is withdrawn via line 4, and the liquid fraction is introduced into a first evaporation unit 5. In the first evaporation unit the lactide-containing liquid fraction is subjected to a first evaporation treatment to obtain a first lactide-containing vaporized stream and a first lactide-containing liquid stream. The first lactide-containing vaporized stream is passed via line 6 to the lower part of the rectification column, whereas the first lactide-containing liquid stream is withdrawn via line 7. In the lower part of the rectification column the first lactide-containing vaporized stream and a lactide-containing liquid fraction are mixed and evaporated to obtain more volatile components and less volatile components. A lactide-containing vaporized fraction which comprises the more volatile components is then withdrawn via line 8 and introduced into a condensation unit 9. Condensate obtained in condensation unit 9 is then passed via line 10 to a melt crystallization unit 11. In the melt crystallization unit 11 a purified lactide-containing stream and a residue stream are obtained. The purified lactide-containing stream is recovered via line 12 and the residue stream is withdrawn from the melt crystallization unit 11 via line 13. Part of the residue stream can be recycled to the bottom part of column 2 via line 14, whereas another part of the residue stream can be introduced into the first evaporation unit 5 via line 15.

Figure 2:
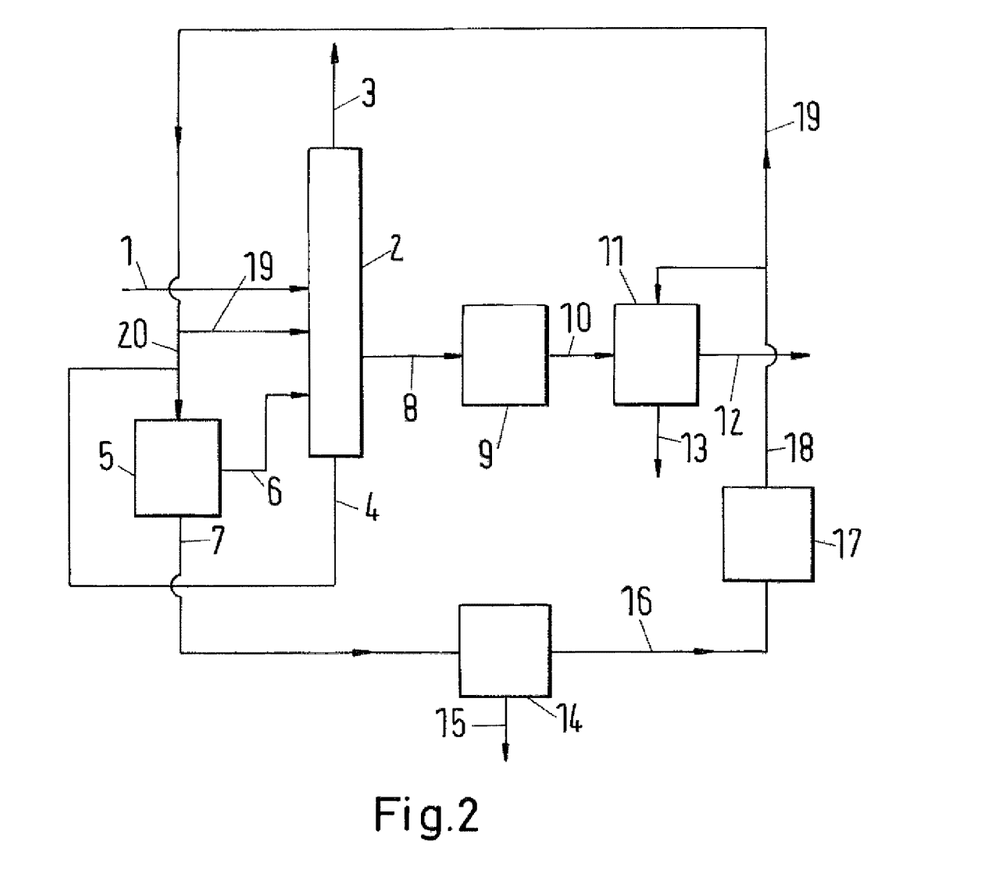

In FIG. 2, a preferred embodiment of the present invention is shown. FIG. 2, differs from FIG. 1 that the first lactide-containing liquid stream as obtained in the first evaporation unit 5 is passed to a second evaporation unit 14 in which it is subjected to a second evaporation treatment. In the second evaporation unit 14 a second lactide-containing vaporized stream and a second lactide-containing liquid stream are obtained. The second lactide-containing liquid stream is withdrawn from the second evaporation unit 14 via line 15, and the second lactide-containing vaporized stream is passed via line 16 to a condensation unit 17. In condensation unit 17 a condensation treatment is carried out to obtain a third lactide-containing liquid stream. The third lactide-containing liquid stream is passed via line 18 to the melt crystallization unit 11. Part of the third lactide-containing liquid stream can be recycled to the bottom part of column 2 via line 19, whereas another part of the third lactide-containing liquid stream can be introduced into the first evaporation unit 5 via line 20.

The more volatile components of the lactide-containing stream to be purified such as water and lactic acid will be more easily evaporated than less volatile components such as liquid lactide, oligomers of lactic acid and other heavy impurities. Hence, the more volatile components, including vapour lactide will move upwards in column 2, whereas the less volatile components will move to the lower part of column 2. The vapour lactide will then be withdrawn from column 2 by means of side draw 8. The upper part of the column is preferably connected to a condensation unit in which the various more volatile components are condensed and subsequently further processed.

In the lower part of the column, a lactide-containing liquid fraction which mainly consists of less volatile components as obtained in step (a) is suitably withdrawn from the column 2 via line 4 and subjected to a first evaporation treatment in a first evaporation unit 5 to obtain a first lactide-containing vapour stream and a first lactide-containing liquid stream. The lactide-containing vapour fraction which is to be condensed in step (b) is at least partly derived from the first lactide-containing vapour stream as obtained from the first evaporation treatment. Preferably, the entire first lactide-containing vapour stream is introduced in the bottom part of column 2. In an alternative embodiment of the present invention, at least part of the first lactide-containing vapour stream by-passes column 2 and is directly introduced into line 8 before it is subjected to the condensation in condensation unit 9. This means that the lactide-containing vapour fraction to be condensed in step (b) will at least partly consist of volatile components such as water, lactic acid and vapour lactide that were present in the first lactide-containing vapour stream. The lactide-containing vapour fraction to be condensed in step (b) will usually also contain volatile components which are derived from mixing and evaporating the lactide-containing liquid fraction which is present in the lower part of the column together with the first lactide-containing vapour stream which is introduced in the bottom part of column 2 via line 6.

The lactide-containing liquid fraction which is subjected to the first evaporation treatment is suitably withdrawn from the bottom of the column or a location in the vicinity thereof via line 4, and passed to a first evaporation unit 5 in which the first evaporation treatment is carried out. The first lactide-containing vapour stream as obtained from the first evaporation unit 5 is suitably introduced into the column 2 via line 6 at a level which is higher than the level at which the lactide-containing liquid fraction was withdrawn from the column. The introduction of the first lactide-containing vapour stream into the column 2 establishes an effective separation of more volatile and less volatile components that are present in the lower part of the column. The more volatile components are withdrawn from the column 2 via line 8 and subjected to step (b).

In the first evaporation treatment water, lactic acid and vapour lactide are suitably separated from liquid lactide, oligomers of lactic acid, catalyst and light and heavy colour impurities.

The present invention therefore also relates to a process for purification of a stream containing a cyclic ester of an alpha-hydroxycarboxylic acid of formula (I)

formula (I)

wherein each R independently represents hydrogen or an aliphatic hydrocarbon having 1 to 6 carbon atoms comprising the steps of:

(a) separating the stream containing the cyclic ester into one or more cyclic ester-containing vapour fractions and one or more cyclic ester-containing liquid fractions;

(a') subjecting a cyclic ester-containing liquid fraction as obtained in step (a) to a first evaporation treatment to obtain a first cyclic ester-containing vapour stream and a first cyclic ester-containing liquid stream;

(b) condensing a cyclic ester-containing vapour fraction as obtained in step (a) and which is at least partly derived from the first cyclic ester-containing vapour stream as obtained in step (a') to obtain a cyclic ester-containing condensate;

(c) subjecting at least part of the cyclic ester-containing condensate as obtained in step (b) to melt crystallization to obtain a purified cyclic ester-containing stream and a residue stream; and (d) recovering the purified cyclic ester-containing stream as obtained in step (c).

The first evaporation treatment in accordance with the present invention is preferably carried out in a falling film evaporation unit. The first evaporation treatment is suitably carried out at a temperature in the range of from 80-200° C., preferably in the range of from 80-180° C., more preferably 100-160° C., and a pressure in the range of from 3-50 mbara, preferably in the range of from 7-20 mbara.

The first evaporation treatment is suitably carried out at a temperature in the range of from 80-180° C. and a pressure in the range of 3-50 mbara. Preferably, the first evaporation treatment is suitably carried out at a temperature in the range of from 100-160° C. and a pressure in the range of 7-20 mbara.

The lactide-containing vapour fraction to be condensed in step (b) is suitably withdrawn from the distillation column via a side draw and introduced into a condensation unit.

Preferably, the side draw is connected to a lower part of the distillation column.

The first lactide-containing liquid stream as obtained from the first evaporation unit can suitably be further processed or recovered. For instance, it can be recycled to an oligomerization reaction in which the lactide-containing stream to be purified is prepared.

The unit in which the condensation is carried out in step (b) can suitably be any type of condensation unit.

Preferably, the condensation unit is a shell and tube or plate heat exchanger in which energy will be removed from the lactide-containing vapour fraction by means of a cooling medium. Non-condensable gases may suitably be sent to a cooling trap or a vacuum pump. In the condensation unit the condensate is preferably undercooled 5 to 10° C. above its freezing point before it is sent to the melt crystallization unit.

The condensation in step (b) can also suitably at least partly be carried out in an internal condenser which is arranged in the lower part of column 2. The condensate so obtained is then withdrawn via side draw 8 and passed to step (c). One skilled in the art will understand that in an alternative embodiment that a direct condensing "internal pump-around" may be used. In yet another embodiment, the lactide-containing vapour fraction to be condensed in step (b) is withdrawn from the distillation column via side draw 8 and a condenser is arranged around side draw 8 which allows the lactide-containing vapour stream to be condensed before it is passed to step (c).

Since in step (b) a lactide-containing vapour fraction, instead of a lactide-containing liquid stream, is subjected to a condensation step prior to melt crystallization, the condensate so obtained will contain less heavy oligomers of lactic acid, catalyst and light and heavy colour impurities. Suitably, the lactide-containing vapour fraction to be condensed in step (b) may contain in the range of from 90-99.9 wt %, preferably in the range of from 95-99.5 wt %, more preferably in the range of from 97-99 wt % of L-lactide, based on the total weight of the lactide-containing vapour fraction to be condensed in step (b). Same results can be obtained with D-lactide. Suitably, the lactide-containing vapour fraction to be condensed in step (b) has a content of meso-lactide in the range of from 0-10 wt %, preferably in the range of from 0-5 wt %, more preferably in the range of from 0-1 wt %, based on the total weight of the lactide-containing vapour fraction to be condensed in step (b).

The condensation in step (b) is suitably carried out at a temperature in the range of from 80-160° C., preferably in the range of from 100-150° C., and a pressure in the range of from 0.005-0.05 bara, preferably in the range of from 0.01-0.03 bara.

At least part of the lactide-containing condensate as obtained in step (b) is subjected in step (c) to melt crystallization to obtain a purified lactide-containing stream and a residue stream.

The purified lactide-containing stream obtained in step (c) may contain in the range of from 98.0-99.98 wt %, preferably in the range of from 99.0-99.95 wt % of L-lactide, based on the total weight of the purified lactide-containing stream. Same results can be obtained with D-lactide. Suitably, the purified lactide-containing stream has a content of meso-lactide in the range of from 0-1 wt %, preferably in the range of from 0-0.5 wt %, based on the total weight of the purified lactide-containing stream. Suitably, the purified lactide-containing stream has 0.1-30 meq/kg of residual acidity, preferably 0.5-6 meq/kg of residual acidity.

Step (c) is suitably carried out in a melt crystallization unit which has a cold surface. Suitably, the melt crystallization is carried out in a continuous mode or a batch mode of operation which is operated in such a way that the melt crystallization unit behaves as a pseudo-continuous unit. The melt crystallization in step (c) can suitably be carried out in one or more crystallization units in series. Any type of melt crystallization unit without the need of a solvent can be used in accordance with the present invention. Suitable examples of melt crystallization sub-units that can be used in the apparatus of the invention include static, falling film, and suspension melt crystallization sub-units, and Suitable examples of melt crystallization stages that can be used in the process of the invention include static, falling film, and suspension melt crystallization stages. In one embodiment of the apparatus use is suitably be made of a falling film crystallization sub-unit, and in one embodiment of the process use is suitably made of a falling film crystallization stage. The skilled person will understand that also various combinations of the different types of melt crystallization sub-units can be used in the apparatus of the invention, and various combinations of the different types of melt crystallization stages can be used in the process of the invention. In other embodiment of the process of the present invention use is made of a combination of a falling film crystallization stage or a suspension melt crystallization stage and a static crystallization stage, allowing a high yield of lactide to be obtained. The inventors have surprisingly found that with such a combined process one can reduce the number of crystallization stages by one or two to get same purity compared to a conventional crystallization process, or, with same number of stages, the combined process will make a better product. Suitably, the melt crystallization in step (c) remains in the range of the crystallization freezing temperature and well below the boiling point of lactide.

The process of the present invention establishes improved kinetics of crystal growth as a result of which less impurities are incorporated into the lactide crystals to be recovered. Impurities will stay in the liquid phase (mother liquor) in the melt crystallization unit and will be removed by means of the residue stream once the crystal growth has been completed.

The residue stream obtained in step (c) is preferably at least partly recycled to step (a). Preferably, the entire residue stream as obtained in step (c) is recycled to step (a).

In a particular attractive embodiment of the present invention, the present process comprises in addition the following steps:

(e) subjecting at least part of the cyclic ester-containing liquid stream as obtained from the first evaporation treatment to a second evaporation treatment to obtain a second cyclic ester-containing vapour stream and a second cyclic ester-containing liquid stream;

(f) subjecting at least part of the second cyclic ester-containing vapour stream as obtained in step (e) to a condensation treatment to obtain a third cyclic ester-containing liquid stream; and (g) subjecting at least part of the third cyclic ester-containing liquid stream as obtained in step (f) to step (a) and/or step (c).

Accordingly, the present invention also relates to a process for purification of a stream containing a cyclic ester of an alpha-hydroxycarboxylic acid of formula (I)

formula (I)

wherein each R independently represents hydrogen or an aliphatic hydrocarbon having 1 to 6 carbon atoms comprising the steps of:

(i) separating the cyclic ester-containing stream into one or more cyclic ester-containing vapour fractions and one or more cyclic ester-containing liquid fractions;

(ii) subjecting a cyclic ester-containing liquid fraction as obtained in step (i) to a first evaporation treatment to obtain a first cyclic ester-containing vapour stream and a first cyclic ester-containing liquid stream.

(iii) condensing a cyclic ester-containing vapour fraction as obtained in step (i) and which is at least partly derived from the first cyclic ester-containing vapour stream as obtained in step (ii) to obtain a cyclic ester-containing condensate;

(iv) subjecting at least part of the cyclic ester-containing condensate as obtained in steps (iii) to melt crystallization to obtain a purified cyclic ester-containing stream and a residue stream;

(v) recovering the purified cyclic ester-containing stream as obtained in step (iv).

(vi) subjecting at least part of the cyclic ester-containing liquid stream as obtained from the first evaporation treatment to a second evaporation treatment to obtain a second cyclic ester-containing vapour stream and a second cyclic ester-containing liquid stream;

(vii) subjecting at least part of the second cyclic ester-containing vapour stream as obtained in step (vi) to a condensation treatment to obtain a third cyclic ester-containing liquid stream; and (viii) subjecting at least part of the third cyclic ester-containing liquid stream as obtained in step (vii) to step (i) and/or step (iv).

The residue stream obtained in step (iv) is preferably at least partly recycled to step (i). Preferably, it is entirely recycled to step (i).

Preferably, the cyclic ester of formula (I) is lactide.

In a preferred embodiment the first lactide-containing liquid stream as obtained in step (ii) is passed to a gas separator before it is subjected to the second evaporation treatment. In the gas separator more volatile components such as water, air, lactic acid and vaporized lactide (dissolved gas) are separated from the first lactide-containing liquid stream. The first lactide-containing liquid stream so obtained is then subjected to the second evaporation treatment in step (e) or step (vi). Suitably, the more volatile components that are separated in the gas separator from the first lactide-containing liquid stream are also subjected to the condensation treatment in step (vii).

Such a gas separator is suitably operated at a temperature in the range of from 80-200° C., preferably in the range of from 80-180° C., more preferably in the range of from 100-160° C., and a pressure in the range of from 3-50 mbara, preferably in the range of from 7-20 mbara.

The gas separator is suitably operated at a temperature in the range of from 80-180° C. and a pressure in the range of 3-50 mbara. Preferably, the gas separator is operated at a temperature in the range of from 100-160° C. and a pressure in the range of 7-20 mbara.

In the second evaporation treatment vaporized lactide is suitably separated from liquid lactide, oligomers of lactic acid and impurities.

Preferably, the second vapour extraction treatment in accordance with the present invention is a wiped film evaporation treatment. The wiped film evaporation unit in which the wiped film evaporation treatment is carried out is preferably a wiped film evaporation unit which comprises an external or internal condenser.

The second evaporation treatment in step (e) or step (vi) is suitably be carried out at a temperature in the range of from 80-200° C., preferably in the range of 100-180° C., more preferably in the range of from 100-160° C., and a pressure in the range of from 3-50 mbara, preferably in the range of from 7-20 mbara.

The second evaporation treatment is suitably carried out at a temperature in the range of from 80-180° C. and a pressure in the range of 3-50 mbara. Preferably, the second evaporation treatment is carried out at a temperature in the range of from 100-160° C. and a pressure in the range of 7-20 mbara.

The second lactide-containing liquid stream as obtained in step (vi) may be further processed. Suitably, the second-lactide-containing liquid stream as obtained in step (vi) is first passed to a receiving tank before it is further processed. At least part of the second lactide-containing liquid stream as contained in the receiving tank may be recycled to step (vi), preferably together with added stream. The remaining part of the second lactide-containing liquid stream will be withdrawn from the receiving tank and may be further processed.

Suitably, the third lactide-containing liquid stream is passed to a receiving tank before at least part of it is subjected to step (i) or step (iv).

In accordance with the present invention a lactide-containing stream of a high purity can be recovered in step (d) or step (v). The recovered lactide-containing stream contains 90-99.9 wt %, preferably 95-99.5 wt %, more preferably 97-99 wt % L-lactide, based on the total weight of the purified lactide-containing stream. Same results can be obtained with D-lactide. The meso-lactide content is suitably in the range of from 0-1 wt %, preferably in the range of 0-0.5 wt %, based on the total weight of the purified lactide-containing stream. Suitably, purified lactide-containing stream to be recovered will have a water content in the range of from 0-100 ppm, preferably in the range of from 0-50 ppm, based on the total weight of the purified lactide-containing stream. Suitably, the purified lactide stream has 0.1-30 meq/kg of residual acidity, preferably 0.5-6 meq/kg of residual acidity.

The purified lactide-containing stream to be recovered in step (d) or step (v) will display a close to transparent appearance. In one embodiment, the purified lactide has a yellowness index according to ASTM E-313-98 of less than or equal to 5, preferably less than or equal to 1, more preferably less than or equal to 0.

The present invention also provides an apparatus in which the present purification process can suitably be carried out.

Accordingly, the present invention also relates to an apparatus for purification of a stream containing a cyclic ester of an alpha-hydroxycarboxylic acid of formula (I)

formula (I)

wherein each R independently represents hydrogen or an aliphatic hydrocarbon having 1 to 6 carbon atoms comprising:

a separation unit (2) which comprises one or more inlets (1), one or more outlets (3, 4), and one or more side draws (8) for withdrawing one or more lactide-containing vaporized fractions from the separation unit (2);

a condensation unit (9) comprising an inlet which is in communication with at least one of the side draws (8), and one or more outlets (10); and a melt crystallization unit (11) comprising an inlet which communicates with at least one of the outlets (10) of the condensation unit (9), and one or more outlets (12, 13).

The separation unit can suitably be any distillation column as described hereinbefore. Preferably, the separation unit is a multi-stage distillation column, more preferably a rectification column.

Preferably, the present apparatus further comprises a first evaporation unit which comprises one or more inlets of which at least one communicates with at least one of the outlets of the separation units, and one or more outlets of which at least one communicates with at least one inlet of the separation unit.

The first separation unit can suitably be a forced circulation evaporator, a plate evaporator, a wiped film evaporator, a circulation evaporator, a fluidized bed evaporator, a falling film evaporator, a counterflow-trickle evaporator, a stirrer evaporator, a wiped film evaporator, a thermal siphon, and a spiral tube evaporator, Preferably, the first evaporation unit is a falling film evaporation unit.

Preferably, the apparatus according to the present invention comprises a second evaporation unit which comprises one or more inlets of which at least one communicates with at least one outlet of the first evaporation unit, and one or more outlets; and a further condensation unit which comprises one or more inlets of which at least one communicates with at least one outlet of the second vapour extraction unit, and one or more outlets of which at least one communicates with an inlet of the melt crystallization unit.

Suitably, the second evaporation unit can be a forced circulation evaporator, a plate evaporator, a circulation evaporator, a fluidized bed evaporator, a falling film evaporator, a counter-flow-trickle evaporator, a stirrer evaporator, a wiped film evaporator, a thermal siphon, and a spiral tube evaporator.

Preferably, the second evaporation unit is a wiped film evaporation unit, more preferably a wiped film evaporation unit comprising an external or internal condenser.

Preferably, at least one of the outlets of the melt crystallization unit is in communication with at least one of the inlets of the separation unit.

The invention is further illustrated my means of the following non-limiting examples.

EXAMPLES

Analysis Methods

In the examples 1 and 2, the lactic acid, the meso-lactide, the L-lactide, the impurities, the L2A and oligomer contents were determined by gas chromatography. The sample was prepared in acetonitril and a silylation step was necessary before injection.

The water content was determined by Karl Fischer.

The residual acidity was determined by colorimetric titration using sodium methoxide as titrant, phenol red as indicator and acetone as solvent.

For the present examples the Yellow Index is a number calculated from spectrophotometric data that describes the change in colour of a test sample from colorless to yellow. According to ASTM methodology, there is a definition of whiteness and yellowness. The ASTM E-313-98 yellowness index is used to determine the degree to which a sample's colour shifts away from an ideal white. In the present case the Yellow Index has been measured on a BYK spectroguide sphere gloss S 6836.

Example 1

Purification Unit

The purification equipment comprises a rectification column packed with the structured packing ROMBOPAK S6M having a total height of 2.7 meters. The packing is a metal sheets packing that yields 3.5 Number of Theoretical stages per Meter with a recommended test mixture according to the European Federation of Chemical Engineering.

The rectification column used in the process of the invention is constituted of:

A top section equipped with a reflux system allowing a total reflux position, and having 1.0 meter of structured packing between the top and the injection point of the crude lactide stream, A medium section from the injection point to the side draw line and having 1.3 meter of structured packing, and A bottom section having 0.4 meter of structured packing. The bottom section is equipped with a reboiling system which is dedicated to convert the liquid stream of crude lactide which is withdrawn into gaseous lactide containing stream, by passing through an evaporation section comprising a falling film evaporator; the vapor phase recovered therefrom being reinjected into the rectification column, while the liquid phase is either passed through a second falling film evaporator, or directly reinjected to the oligomerization unit.

The vapor containing lactide stream withdrawn from the side draw is sent to a condenser and then finally to the melt crystallization unit.

Purification Operation

The crude lactide stream, the composition of which is given in Table 1 was injected into the rectification column at a rate of 6.61 kg/h, at a temperature of 114° C. and was subjected to distillation conditions.

A distillate of 0.19 kg/h was removed from the top of the column, the composition of which is given in Table 2.

TABLE 1

Lactic acid: 0.87%
Meso-lactide: 2.89%
L-lactide: 88.28%
Impurities: 0.51%
L2A: 2.07%
Oligomer: 5.38%
Yellow Index: 14.2

TABLE 2

Lactic Acid: 24.96%
Meso-lactide: 20.67%
L-lactide: 42.32%
Impurities: 8.48%
L2A: 2.47%
Oligomer: 1.10%
Yellow Index: 10.0

The term L2A means linear lactic acid dimmer.

A bottom product was withdrawn from the bottom of the first evaporation unit (7) at a rate of 2.32 kg/h and at a temperature of 151° C.

The gaseous lactide stream withdrawn from the side draw of the rectification column, at a rate of 4.10 kg/h and at a temperature of 133° C. was then directly injected into the condenser. The composition of the product recovered as condensate from the condenser is given in Table 3.

TABLE 3

Lactic acid: 0%
Meso-lactide: 2.5%
L-lactide: 97.27%
Impurities: 0%
L2A: 0.23%
Oligomer: 0%
Water: 214 ppm
Residual acidity: 33.2 mEq/kg
Yellow Index: minus 1.2 (−1.2)

The lactide stream recovered from the condenser was directly sent to the melt crystallization unit.

The used crystallizer was a falling film crystallizer, equipped with one industrial scale tubular crystallizer element. Three falling film purification stages were performed successively, the analysis of the samples from each stage showed that actually two stages were sufficient to obtain a product having the desired purity. The residue stream withdrawn from the melt crystallization unit was subjected to a stripping stage in either a falling film crystallizer and/or a static crystallizer.

After the two stages of purification, we recovered a lactide containing product comprising 99.83% L-lactide, 0.14% meso-lactide, 0.03% lactic acid, no impurities and no L2A, but only 28.3 ppm water and a residual acidity of 1.43 mEq/kg.

The yellow index of the product so recovered was of minus 2.7 (−2.7). This product is convenient for the polymerization into PLA. In addition the obtained lactide so purified has good coloration as well as a very small water content.

Example 2

The same crude lactide stream as in Example 1 has been used and treated on the same rectification packed column under the same operating conditions such as described in example 1 except that the bottom product has been treated differently.

So, the liquid lactide stream recovered after the first evaporation unit (7) was sent to a second evaporation unit (14), the gaseous lactide stream recovered from said second evaporation unit, which was constituted of a wiped film evaporator, was sent to the condenser (17).

The condensate product after said condenser (17) was constituted of 95.83% of L-LD and the condensate flow rate coming out from said condenser was of 0.35 kg/h. In other terms, such an operation gave a gain of 8.41% in yield over that of example 1 operating without said second evaporation unit.

This lactide containing product was sent to the melt crystallization unit (11), together with the lactide containing stream coming from the condenser side draw (9) and having the composition as described in example 1.

In the crystallization unit (11), four stages were carried out in a falling film crystallization sub-unit (including a stripping stage) and one stage in a static crystallization sub-unit. After the purification of both lactide containing streams under melt crystallization, a final lactide was recovered after two purification stages containing product comprising 99.82% L-Lactide, 0.14% meso-lactide, 0.04% lactic acid, no impurities and no L2A, but only 30.2 ppm water and a residual acidity of 1.49 mEq/kg.

The Yellow Index of the product so recovered was of minus 2.6 (−2.6).

The product is convenient for the polymerization into PLA.

The invention claimed is:

1. An apparatus for purification of a stream containing a cyclic ester of an alpha-hydroxycarboxylic acid of formula (I)

formula (I)

wherein each R independently represents hydrogen or an aliphatic hydrocarbon having 1 to 6 carbon atoms comprising:
  a separation unit which is a distillation column and comprises one or more separation unit inlets, one or more separation unit outlets, and one or more side draws for withdrawing one or more cyclic ester-containing vapour fractions from the separation unit;
  a condensation unit comprising a condensation unit inlet which is in communication with at least one of the one or more side draws of the separation unit, and one or more condensation unit outlets; and
  a melt crystallization unit comprising a melt crystallization unit inlet which communicates with at least one of the condensation unit outlets, and one or more melt crystallization unit outlets.

2. The apparatus according to claim 1, further comprising a first evaporation unit which comprises one or more first evaporation unit inlets of which at least one communicates with at least one of the one or more separation unit outlets, and one or more first evaporation unit outlets of which at least one communicates with at least one separation unit inlet.

3. The apparatus according to claim 2, wherein the first evaporation unit is a falling film evaporation unit.

4. The apparatus according to claim 2, comprising a second evaporation unit which comprises one or more second evaporation unit inlets of which at least one communicates with at least one first evaporation unit outlet, and one or more second evaporation unit outlets; and a further condensation unit which comprises one or more further condensation unit inlets of which at least one communicates with at least one second evaporation unit outlet, and one or more further condensation unit outlets of which at least one communicates with a melt crystallization unit inlet of the melt crystallization unit.

5. The apparatus according to claim 4, wherein the second evaporation unit is a wiped film evaporation unit.

6. The apparatus according to claim 1, wherein at least one of the one or more melt crystallization unit outlets is (in communication with at least one of the one or more separation unit inlets.

7. A process for purification of a stream containing a cyclic ester of an alpha-hydroxycarboxylic acid of formula (I)

formula (I)

wherein each R independently represents hydrogen or an aliphatic hydrocarbon having 1 to 6 carbon atoms comprising:

providing the apparatus of claim 1 and using it in a process comprising the steps of:

(a) separating the cyclic ester-containing stream into one or more cyclic ester-containing vapour fractions and one or more cyclic ester-containing liquid fractions;

(b) condensing a cyclic ester-containing vapour fraction as obtained in step (a) to obtain a cyclic ester-containing condensate;

(c) subjecting at least part of the cyclic ester-containing condensate as obtained in step (b) to melt crystallization to obtain a purified cyclic ester-containing stream and a residue stream; and (d) recovering the purified cyclic ester-containing stream as obtained in step (c).

8. The process according to claim 7, wherein the cyclic ester is lactide.

9. The process according to claim 7, wherein the cyclic ester-containing condensate is undercooled in step (b) 5 to 10° C. above its freezing point before it is subjected to melt crystallization in a step (c).

10. The process according to claim 7, wherein the cyclic ester-containing vapour fraction to be condensed in step (b) is withdrawn from the distillation column via a side draw and introduced into a condensation unit.

11. The process according to claim 7, wherein a cyclic ester-containing liquid fraction as obtained in step (a) is subjected to a first evaporation treatment to obtain a first cyclic ester-containing vapour stream and a first cyclic ester-containing liquid stream, and wherein the cyclic ester-containing vapour fraction which is to be condensed in step (b) is at least partly derived from the first cyclic ester-containing vapour stream as obtained from the first evaporation treatment.

12. The process according to claim 11, wherein the first evaporation treatment is a falling film evaporation treatment.

13. The process according to claim 11, comprising in addition the following steps:

(e) subjecting at least part of the cyclic ester-containing liquid stream as obtained from the first evaporation treatment to a second evaporation treatment to obtain a second cyclic ester-containing vapour stream and a second cyclic ester-containing liquid stream;

(f) subjecting at least part of the second cyclic ester-containing vapour stream as obtained in step (e) to a condensation treatment to obtain a third cyclic ester-containing liquid stream; and (g) subjecting at least part of the third cyclic ester-containing liquid stream as obtained in step (0 to step (a) and/or step (c).

14. The process according to claim 13, wherein in the second evaporation treatment vapour cyclic ester is separated from liquid cyclic ester, oligomers of alpha-hydroxycarboxylic acid and other impurities.

15. The process according to claim 13, wherein the second evaporation treatment is a wiped film evaporation treatment.

16. The process according to claim 7, wherein at least part of the residue stream as obtained in step (c) is recycled to step (a).

17. The process according to claim 7, wherein a combination of a falling film crystallization stage or a suspension melt crystallization stage and a static crystallization stage are employed in step (c).

18. A method for using the apparatus according to claim 1, comprising the steps of providing the apparatus of claim 1 and using it in the purification of a stream containing a cyclic ester of an alpha-hydroxycarboxylic acid of formula (I)

formula (I)

wherein each R independently represents hydrogen or an aliphatic hydrocarbon having 1 to 6 carbon atoms.

* * * * *